(12) United States Patent
Sakura et al.

(10) Patent No.: US 6,329,556 B1
(45) Date of Patent: Dec. 11, 2001

(54) PROCESS FOR PREPARING BISPHENOL A

(75) Inventors: Katsuhiko Sakura; Shingo Ueda, both of Kitakyushu; Genki Takeuchi; Shyouta Shirasaka, both of Oita; Toshikazu Maruyama, Kitakyushu; Yasuharu Hukuda, Kitakyushu; Taketoshi Kitoh, Kitakyushu; Morio Kimura, Kitakyushu, all of (JP)

(73) Assignee: Nippon Steel Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/701,485
(22) PCT Filed: Jun. 23, 1999
(86) PCT No.: PCT/JP99/03348
§ 371 Date: Nov. 29, 2000
§ 102(e) Date: Nov. 29, 2000
(87) PCT Pub. No.: WO00/00454
PCT Pub. Date: Jan. 6, 2000

(30) Foreign Application Priority Data

Jun. 26, 1998 (JP) .................................................. 10-196540

(51) Int. Cl.[7] .................................................. C07C 39/16
(52) U.S. Cl. .............................. 568/728; 568/727; 521/33
(58) Field of Search ..................................... 568/728, 727; 521/33

(56) References Cited

U.S. PATENT DOCUMENTS

| 2,366,007 | * | 12/1944 | D'Alelio | 521/33 |
| 2,462,555 | * | 2/1949 | Rosenthal | 521/33 |
| 6,221,248 | * | 4/2001 | Lin | 210/500.34 |

FOREIGN PATENT DOCUMENTS

| 2-32032 | | 2/1990 | (JP) . |
| 6-32755 | | 2/1994 | (JP) . |
| 6-320009 | | 11/1994 | (JP) . |
| 8-269137 | | 10/1996 | (JP) . |
| 10-139696 | | 5/1998 | (JP) . |
| 11-179218-A | * | 7/1999 | (JP) . |

* cited by examiner

*Primary Examiner*—Michael L. Shippen
(74) *Attorney, Agent, or Firm*—Birch, Stewart, Kolasch & Birch, LLP

(57) ABSTRACT

This invention relates to a process for preparing bisphenol A by the condensation of phenol with acetone in the presence of cation exchange resin obtained by sulfonating copolymers of monovinyl monomers mainly consisting of styrenes and divinyl monomers as crosslinking agent while using divinylbiphenyl and divinylbenzene mainly as said divinyl monomers and controlling the molar ratio of divinylbiphenyl to divinylbenzene at 10/0–2/8. The cation exchange resin to be used as catalyst in the condensation reaction shows a long life, maintains the production of bisphenol A over a long period of time, possesses high strength and is useful for economical and advantageous production of bisphenol A.

2 Claims, No Drawings

PROCESS FOR PREPARING BISPHENOL A

This application is the national phase under 35 U.S.C. §371 of PCT International Application No. PCT/JP99/03348 which has an International filing date of Jun. 23, 1999, which designated the United States of America.

FIELD OF TECHNOLOGY

This invention relates to a process for preparing 2,2-bis (4-hydroxyphenyl)propane (hereinafter referred to as bisphenol A).

BACKGROUND TECHNOLOGY

In recent years, there is an increasing demand for bisphenol A as a principal raw material for engineering plastics such as polycarbonates and epoxy resins. Bisphenol A is usually obtained by the reaction of excess phenol with acetone in the presence of an acidic catalyst. Cation exchange resins are most common for such catalyst and those containing sulfonic acid groups are normally used. Of cation exchange resins containing sulfonic acid groups, sulfonated styrene-divinylbenzene copolymers are put to practical use most widely.

Sulfonated styrene-divinylbenzene copolymers are resins obtained by copolymerizing styrene and divinylbenzene in the presence of a polymerization initiator and introducing sulfonic acid groups to the aromatic rings of the styrene and divinylbenzene in the resulting copolymers with the aid of sulfuric acid and the like. The copolymers in question are considered to have a complex three-dimensional network in which divinylbenzene bridges polystyrene chains to form an irregularly intertwined structure. An increase in the amount of divinylbenzene leads to increased branching of the polystyrene chain and a denser network. Conversely, a decrease in the amount of divinylbenzene leads to decreased branching and a coarser network. The divinylbenzene here plays the role of a knot in the network and is referred to as crosslinking agent. The ratio of the amount of crosslinking agent added to the amount of total monomers used is generally designated as degree of crosslinking.

The aforementioned copolymers ranging widely in the degree of crosslinking have been used as a catalyst for the preparation of bisphenol A and the existence of a significant correlation has been reported between the degree of crosslinking and the catalyst life. For example, Japan Kokai Tokkyo Koho Hei 6-32755 (1994) teaches the use of cation exchange resins with a degree of crossliking of 6 wt. % or less since the life of a cation exchange resin catalyst becomes longer as the degree of crosslinking becomes lower. However, a cation exchange resin catalyst with a lower degree of crosslinking generally contains less sulfonic acid groups per unit volume of catalyst and leads to reduced output of bisphenol A. Moreover, a cation exchange resin catalyst with a lower degree of crosslinking is more susceptible to elastic deformation when subjected to a stress from the outside and, when used in a fixed-bed reactor, may occasionally cause such pressure loss as to render the production difficult on a commercial scale. Thus, elongation of the catalyst life by reducing the degree of crosslinking causes another problem and an improved procedure is desired for development of cation exchange resin catalysts which maintain the production of bisphenol A over a long period of time, resist elastic deformation and possess high strength without decreasing the number of sulfonic acid groups per unit volume of catalyst.

An object of this invention is to provide cation exchange resin catalysts which show high productivity per unit volume of catalyst, have a long life, maintain high productivity of bisphenol A over a long period of time, resist elastic deformation and possess high strength. Another object of this invention is to provide an efficient process for preparing bisphenol A.

DISCLOSURE OF THE INVENTION

The present inventors have conducted intensive studies to accomplish the aforementioned objective, found that divinylbiphenyl is appropriate for use as crosslinking agent for cation exchange resin catalysts and arrived at this invention.

Accordingly, this invention relates to a process for preparing 2,2-bis(4-hydroxyphenyl)propane by the condensation of phenol with acetone in the presence of a cation exchange resin catalyst obtained by sulfonating copolymers of monovinyl monomers mainly comprising of styrenes and divinyl monomers as crosslinking agent which comprises using divinyl monomers containing 20 mol % or more of divinybiphenyl. This invention also relates to the aforementioned cation exchange resin catalysts to be used in the condensation reaction.

The sulfonated copolymers of styrene and divinyl monomers to be used as cation exchange resin catalyst in this invention are prepared in accordance with a known procedure by copolymerizing a mixture of monovinyl monomers mainly comprising of styrenes and divinyl monomers mainly comprising of divinylbiphenyl or divinylbenzene and divinylbiphenyl in the presence of a polymerization initiator and sulfonating the resulting copolymers with sulfuric acid or the like to introduce sulfonic acid groups to the aromatic rings of the styrenes and divinyl monomers.

Styrenes include monovinyl derivatives of aromatic compounds such as styrene, vinyltoluene, a -methylstyrene, vinylxylene, vinylethylbenzene, vinylbiphenyl, methylvinylbiphenyl. Monovinyl monomers other than styrenes include aliphatic olefins. Monovinyl monomers here mainly consist of styrenes, that is, they consist of 50 mol % or more, preferably 80 mol % or more of styrenes.

Divinyl monomers may be 100% divinylbiphenyl or a mixture of divinylbiphenyl with other divinyl monomers if the latter are less than 20 mol %. Such other divinyl monomers include divinylbenzene and divinyltoluene, divinylbenzene being preferable. Divinylbiphenyl accounts for 20 mol % or more, preferably 50 mol % or more, of divinyl monomers. Moreover, divinyl monomers mainly consist of divinylbiphenyl and divinylbenzene and the two together desirably account for 50 mol % or more, preferably 80 mol % or more, of divinyl monomers.

Of several isomers of divinylbiphenyl, 4,4'-divinylbiphenyl or a mixture of isomers mainly consisting of 4,4'-divinylbiphenyl is preferable. Depending on the procedure used for its preparation, 4,4'-divinylbiphenyl occasionally contains the unreacted starting material and intermediates such as 4,4'-diethylbiphenyl, 4,4'-vinylethylbiphenyl and 4-vinylbiphenyl and it can be used together with such intermediates without ill effect. Rather, it is desirable that 4,4'-divinylbiphenyl contains 10–60 mol % of monovinylbiphenyls such as 4,4'-vinylethylbiphenyl and 4-vinylbiphenyl. Monovinylbiphenyls are counted as monovinyl monomer. Likewise, of the isomers of divinylbenzene, 1,4-divinylbenzene or a mixture mainly consisting of 1,4-divinylbenzene is preferable.

As for the ratio of divinylbenzene to divinylbiphenyl in use, more divinylbiphenyl gives a longer catalyst life and higher catalyst strength, which makes it desirable to use as high a proportion of divinylbiphenyl as possible. Concretely, the molar ratio of divinylbiphenyl to divinylbenzene is 10/0–8/2, preferably 10/0–5/5.

The degree of crosslinking, as designated by the weight ratio of divinyl monomers as crosslinking agent to a mixture of all monomers, is not restricted, but it is 0.1–20 wt. %, preferably 1–15 wt. %, more preferably 2–8 wt. %, in consideration of the catalyst life, productivity of bisphenol A and catalyst strength. The degree of crosslinking as designated by the molar ratio of divinyl monomers to the total monomers is 2–50 mol %, preferably 2–40 mol %, more preferably 3–10 mol %. A decrease in this degree of crosslinking lowers the catalyst strength and performance.

A known procedure can be adopted for the copolymerization of monovinyl monomers mainly consisting of styrenes and divinyl monomers. Normally, the copolymerization is carried out at 50–90° C. for 3–30 hours in accordance with a procedure, for example, of introducing water and a dispersant in specified amounts to the polymerization reactor, adding a mixture of monomers in which a polymerization initiator has been dissolved to the water with stirring to form an oil-in-water suspension, and carrying out the polymerization at a specified temperature in a nitrogen atmosphere.

A concrete procedure for the polymerization is as follows. A polymerization initiator is added to a mixture of monovinyl monomers and divinyl monomers and the resulting mixture is subjected to mass, solution or suspension polymerization. Suspension polymerization is preferable for the preparation of resin beads suitable for use in a fixed bed. In this case, water in an amount 1–10 times that of the monomer mixture is used as dispersing medium and a dispersant such as polyvinyl alcohol and carboxymethylcellulose is used in an amount 0.05–5 wt. % of the monomer mixture. As for polymerization initiator, a known substance such as benzoyl peroxide and an azo compound can be used in an amount 0.01–15 wt. % of the monomer mixture.

Those copolymers which are prepared by merely copolymerizing monovinyl monomers mainly consisting of styrenes and divinyl monomers as crosliking agent are transparent and gel-like in structure and they are called gel type resins. The copolymers in question form a two-dimensional network in which bifunctional divinyl monomers bridge polystyrene chains to form an irregularly intertwined structure and the interstices in the network are called micropores.

On the other hand, copolymers may be prepared in another way by copolymerizing a solution of monovinyl monomers mainly consisting of styrenes and divinyl monomers as crosslinking agent in an organic solvent which is a good solvent of these monovinyl and divinyl monomers and insoluble in water (for example, toluene, ethylbenzene and n-hexane) and stripping the organic solvent. A large space nearly free of intertwinement is created inside the resulting copolymers or the copolymers are porous. Such copolymers are generally called macroporous resins and the large space is called macropore.

Gel type or macroporous copolymers prepared in the aforementioned manner normally occur as crack-free spherical beads with a particle diameter in the range 100–1,000 μm. The beads are sulfonated by a given sulfonating agent in the presence of a swelling agent to yield cation exchange resin catalysts.

Preferable as a swelling agent is an organic solvent that swells the aforementioned copolymers well and is inert to the sulfonating agent; for example, dichloromethane and nitrobenzene. Such a solvent is normally used in an amount 0.1–10 times that of the copolymers on a weight basis.

The sulfonation is effected by stirring the swollen copolymer particles in 95–100% sulfuric acid. The amount of sulfuric acid is normally 3–30 times that of the copolymers on a weight basis. The temperature for the treatment is 50–150° C., preferably 90–110 ° C., and the period is 3–30 hours.

The sulfonated styrene-divinyl monomer copolymers, that is, cation exchange resins, obtained in the aforementioned manner are used as catalyst in this invention. This cation exchange resin catalyst is generally used in a fixed-bed reactor, but it may be used in a fluidized-bed reactor.

For the preparation of bisphenol A, a known procedure involving the use of cation exchange resin as catalyst may be adopted. The raw materials for the reaction are usually acetone and excess phenol and, if necessary, a reaction accelerator may be additionally used. As for the raw material acetone, a commercially available material is used as it is here but the acetone remaining unreacted in the reaction mixture may be recovered by such means as distillation and used.

As for the raw material phenol, phenol of industrial grade available on the market is used as it is or the mother liquor obtained by crystallizing the adduct of bisphenol A with phenol from the reaction mixture and separating the crystals by filtration may be used. Useful as reaction accelerator are thiols such as methylmercaptan, ethylmercaptan, mercaptoethanol and mercaptopropionic acid.

In case the aforementioned cation exchange resin is used as catalyst in a fixed-bed reactor according to the process of this invention, the liquid hourly space velocity (LHSV) is 0.1–20 hr$^{-1}$, preferably 0.3–5 hr $^{-1}$. As for the reaction temperature, the formation of impurities originating from side reactions becomes pronounced at high temperatures and such impurities adversely affect the quality of bisphenol A while the rate of reaction drops to cause a decrease in the output of bisphenol A at low temperatures. Concretely, the reaction temperature is preferably 45–140 ° C., more preferably 55–100° C. The molar ratio of acetone to phenol is normally 0.005–0.5, preferably 0.01–0.3. A reaction accelerator may be added at a rate of 0.01–2% of the raw materials.

A general procedure for recovering bisphenol A from the reaction mixture is to separate low-boiling substances such as acetone, water, and reaction accelerator from the reaction mixture by such means as distillation, crystallize the adduct of bisphenol A with phenol, separate the crystalline adduct from the mother liquor by such means as filtration, and remove the phenol from the adduct.

PREFERRED EMBODIMENTS OF THE INVENTION

EXAMPLE 1

Into a 500-ml three-necked separable flask fitted with a stirrer and a condenser was introduced 0.1 g of polyvinyl alcohol, then was introduced a mixture of 44.1 g of styrene, 5.9 g of crosslinking agents containing 52% of divinylbiphenyl (mainly consisting of the 4,4'-isomer; % by weight here and hereafter), 30% of vinylethylbiphenyl and 18% of vinylbiphenyl and 0.1 g of benzoyl peroxide, and the mixture was allowed to polymerize with stirring at 80 ° C. for 10 hours while passing nitrogen through the system.

Particles of the copolymers were recovered from the mixture after polymerization, 30 g of the air-dried particles was placed in a 300-ml four-necked flask fitted with a stirrer and a condenser, 60 g of water and 150 g of nitrobenzene were added, and the resulting mixture was stirred at 70° C. for 2 hours to swell the copolymers. The swollen copolymers were recovered and air-dried, placed in whole in a 300-ml four-necked flask fitted with a stirrer and a condenser, 150 g of concentrated sulfuric acid was added to the flask, and the mixture was heated at 80° C. for 10 hours with stirring to effect sulfonation. After the reaction, the sulfonated copolymers were collected by filtration and washed with 1,200 g of water.

The cation exchange resin containing sulfonic acid groups obtained in this manner showed a total exchange capacity of 1.31 meq/ml-R. The chatillon value was 440 g/particle as a result of the crushing test conducted on 100 resin particles with a diameter of 600 μm.

Using the aforementioned cation exchange resin containing sulfonic acid groups as a catalyst, the reaction for the preparation of bisphenol A was carried out as follows. Phenol was allowed to react with acetone in the presence of ethylmercaptan as a reaction accelerator to yield a mixture containing bisphenol A, low-boiling substances such as acetone, water and ethylmercaptan were distilled off from the mixture, the adduct of bisphenol A with phenol was crystallized out and filtered off to give the mother liquor (composed of 85% of phenol, 8% of bisphenol A, 5% of 2,4-isomer, and 2% of other impurities), 1,000 parts by weight of which was mixed with 30 parts by weight of acetone and 2 parts by weight of ethylmercaptan and fed continuously at a rate of 50 ml/hr at 70 ° C. to a flow reactor that is made of stainless steel, 1 cm in inside diameter and filled with 50 ml of the aforementioned cation exchange resin. Table 1 shows the change in conversion of acetone with time in terms of conversion of acetone vs. number of days of feeding to the flow reactor and also the pressure loss in the reactor after 150 days of feeding.

EXAMPLE 2

The procedure of Example 1 was followed to prepare cation exchange resin containing sulfonic acid groups except using a feedstock containing 44.6 g of styrene, 4.7 g of crosslinking agents composed of 52% of divinylbiphenyl, 30% of vinylethylbiphenyl and 18% of vinylbiphenyl and 0.7 g of crosslinking agents composed of 57% of divinylbenzene and 43% of vinylethylbenzene in the step for preparing the copolymers. The resin showed a total exchange capacity of 1.29 meq/ml-R and also a chatillon value of 430 g/particle as a result of the crushing test conducted on 100 resin particles with a diameter of 600 μm.

EXAMPLE 3

The procedure of Example 1 was followed to prepare cation exchange resin containing sulfonic acid groups except using a feedstock containing 45.5 g of styrene, 2.4 g of crosslinking agents composed of 52% of divinylbiphenyl, 30% of vinylethylbiphenyl and 18% of vinylbiphenyl and 2.1 g of crosslinking agents composed of 57% of divinylbenzene and 43% of vinylethylbenzene in the step for preparing the copolymers. The resin showed a total exchange capacity of 1.28 meq/ml-R and also a chatillon value of 420 g/particle as a result of the crushing test conducted on 100 resin particles with a diameter of 600 μm.

EXAMPLE 4

The procedure of Example 1 was followed to prepare cation exchange resin containing sulfonic acid groups except using a feedstock containing 45.9 g of styrene, 1.3 g of crosslinking agents composed of 52% of divinylbiphenyl, 30% of vinylethylbiphenyl and 18% of vinylbiphenyl and 2.8 g of crosslinking agents composed of 57% of divinylbenzene and 43% of vinylethylbenzene in the step for preparing the copolymers. The resin showed a total exchange capacity of 1.27 meq/ml-R and also a chatillon value of 440 g/particle as a result of the crushing test conducted on 100 resin particles with a diameter of 600 μm.

Comparative Example 1

The procedure of Example 1 was followed to prepare cation exchange resin containing sulfonic acid groups except using a feedstock containing 46.2 g of styrene, 0.6 g of crosslinking agents composed of 52% of divinylbiphenyl, 30% of vinylethylbiphenyl and 18% of vinylbiphenyl and 3.2 g of crosslinking agents composed of 57% of divinylbenzene and 43% of vinylethylbenzene in the step for preparing the copolymers. The resin showed a total exchange capacity of 1.25 meq/ml-R and also a chatillon value of 390 g/particle as a result of the crushing test conducted on 100 resin particles with a diameter of 600 μm.

Comparative Example 2

The procedure of Example 1 was followed to prepare cation exchange resin containing sulfonic acid groups except using a feedstock containing 46.5 g of styrene and 3.5 g of crosslinking agents composed of 57% of divinylbenzene and 43% of vinylethylbenzene in the step for preparing the copolymers. The resin showed a total exchange capacity of 1.24 meq/ml-R and also a chatillon value of 380 g/particle as a result of the crushing test conducted on 100 resin particles with a diameter of 600 μm.

The cation exchange resins containing sulfonic acid groups obtained in Examples 2 to 4 and Comparative Examples 1 and 2 were respectively used as catalyst in the reaction in the manner described in Example 1.

Table 1 shows the molar ratio of divinylbiphenyl to divinylbenzene (DVBP/DVB), chatillon value, total exchange capacity per 1 ml of swollen resin of the cation exchange resins and the reaction results in the aforementioned Examples and Comparative Examples.

TABLE 1

| | DVBP/ DVB | Chatillon value | Total exchange | Conversion of acetone | | | Pressure |
|---|---|---|---|---|---|---|---|
| | Molar ratio | g/particle | capacity meq/ml-R | 0 day | 30 days | 150 days | loss kg/cm² |
| Example 1 | 10/0 | 440 | 1.31 | 93.1 | 92.2 | 88.5 | 4.5 |
| Example 2 | 8/2 | 430 | 1.29 | 92.4 | 90.1 | 81.4 | 4.6 |
| Example 3 | 4/6 | 420 | 1.28 | 91.1 | 86.3 | 66.5 | 4.8 |
| Example 4 | 2/8 | 400 | 1.27 | 90.5 | 84.3 | 59.1 | 5.0 |
| Comparative example 1 | 1/9 | 390 | 1.25 | 90.1 | 83.4 | 55.6 | 5.5 |
| Comparative example 2 | 0/10 | 380 | 1.24 | 89.7 | 82.0 | 52.4 | 5.6 |

Industrial Applicability

Catalysts based on the cation exchange resins containing sulfonic acid groups developed by this invention show not only a longer life than those based on cation exchange resins containing sulfonic acid groups derived from the conventional styrene-divinylbenzene copolymers but also a reduced pressure loss when used in a flow reactor and they are capable of improving further the productivity of bisphenol A.

What is claimed is:

1. A process for preparing 2,2-bis(4-hydroxypheyl)propane by the condensation of phenol with acetone in the presence of cation exchange resin obtained by sulfonating copolymers of monovinyl monomers mainly comprising of styrenes and divinyl monomers as crosslinking agent which comprises using divinylbiphenyl or divinylbiphenyl and divinylbenzene mainly as said divinyl monomers and controlling the molar ratio of divinylbiphenyl to divinylbenzene at 10/0–2/8.

2. Catalysts for preparing 2,2-bis(4-hydroxyphenyl)propane which are composed of cation exchange resins useful for the condensation of phenol with acetone to yield 2,2-bis(4-hydroxyphenyl)propane and are prepared by sulfonating copolymers of monovinyl monomers mainly comprising of styrenes and divinyl monomers as crosslinking agent while using divinylbiphenyl or divinylbiphenyl and divinylbenzene mainly as said divinyl monomers and controlling the molar ratio of divinylbiphenyl to divinylbenzene at 10/0–2/8.

* * * * *